(12) United States Patent
Moskal

(10) Patent No.: US 11,996,203 B2
(45) Date of Patent: May 28, 2024

(54) SYSTEMS AND METHODS FOR CONTROLLING A PLURALITY OF DRUG LIBRARIES

(71) Applicant: Fresenius Vial SAS, Brézins (FR)

(72) Inventor: Witold Moskal, Park Ridge, IL (US)

(73) Assignee: Fresenius Vial SAS, Brézins (FR)

( * ) Notice: Subject to any disclaimer, the term of this patent is extended or adjusted under 35 U.S.C. 154(b) by 755 days.

(21) Appl. No.: 17/054,911

(22) PCT Filed: Apr. 4, 2019

(86) PCT No.: PCT/EP2019/058493
§ 371 (c)(1),
(2) Date: Nov. 12, 2020

(87) PCT Pub. No.: WO2019/219291
PCT Pub. Date: Nov. 21, 2019

(65) Prior Publication Data
US 2021/0225527 A1 Jul. 22, 2021

Related U.S. Application Data

(60) Provisional application No. 62/671,350, filed on May 14, 2018.

(51) Int. Cl.
*G16H 70/40* (2018.01)
*A61M 5/14* (2006.01)
(Continued)

(52) U.S. Cl.
CPC .......... *G16H 70/40* (2018.01); *A61M 5/1407* (2013.01); *A61M 5/142* (2013.01); *G16H 20/17* (2018.01);
(Continued)

(58) Field of Classification Search
CPC ..... G16H 70/40; G16H 20/17; A61M 5/1407; A61M 5/142; A61M 2005/14208; A61M 2205/52
(Continued)

(56) References Cited

U.S. PATENT DOCUMENTS 5,681,285 A * 10/1997 Ford ..................... A61M 5/172
604/67
10,463,788 B2 * 11/2019 Day ....................... G16H 40/40
(Continued)

FOREIGN PATENT DOCUMENTS

| EP | 2410448 | 1/2012 |
|---|---|---|
| EP | 2759979 | 7/2014 |

(Continued)

OTHER PUBLICATIONS

Breland, Burnis, Continuous quality improvement using intelligent infusion pump data analysis, Am. J. of Health-System Pharm., vol. 67, pp. 1446-1455 (Sep. 1, 2010).
(Continued)

*Primary Examiner* — Ronald D Hartman, Jr.
(74) *Attorney, Agent, or Firm* — Cook Alex Ltd.

(57) ABSTRACT

A system for controlling a plurality of drug libraries includes a computing device on which is stored a master drug library, the master drug library comprising a plurality of drug definitions. The system also includes a plurality of programmable patient devices coupled to the server, each patient device having an individual drug library stored thereon, the individual drug library comprising a reference only to at least one of the drug definitions in the master drug library. In addition, a method for controlling a plurality of drug libraries includes storing on a computing device a master drug library, the master drug library comprising a plurality of drug definitions. The method also includes storing on
(Continued)

each of a plurality of programmable patient devices an individual drug library, the individual drug library comprising a reference only to at least one of the drug definitions in the master drug library.

10 Claims, 7 Drawing Sheets

(51) Int. Cl.
 *A61M 5/142* (2006.01)
 *G16H 20/17* (2018.01)
(52) U.S. Cl.
 CPC ............. *A61M 2005/14208* (2013.01); *A61M 2205/52* (2013.01)
(58) Field of Classification Search
 USPC .......................................................... 700/90
 See application file for complete search history.

(56) References Cited

U.S. PATENT DOCUMENTS

| 11,344,673 | B2 * | 5/2022 | Lindo | A61M 5/16827 |
| 2005/0144043 | A1 * | 6/2005 | Holland | G16H 70/40 |
| | | | | 705/3 |
| 2005/0177096 | A1 * | 8/2005 | Bollish | A61B 5/032 |
| | | | | 604/65 |
| 2005/0224083 | A1 * | 10/2005 | Crass | G16H 70/40 |
| | | | | 128/897 |
| 2011/0264043 | A1 * | 10/2011 | Kotnik | A61P 29/00 |
| | | | | 514/629 |
| 2011/0264044 | A1 * | 10/2011 | Bartz | A61M 5/145 |
| | | | | 604/151 |
| 2015/0343141 | A1 | 12/2015 | Lindo et al. | |
| 2016/0339167 | A1 | 11/2016 | Ledford et al. | |
| 2016/0350513 | A1 * | 12/2016 | Jacobson | A61M 5/172 |
| 2018/0122502 | A1 * | 5/2018 | Jones | G16H 50/20 |
| 2018/0147347 | A1 * | 5/2018 | Drost | A61M 5/172 |

FOREIGN PATENT DOCUMENTS

| WO | WO 2007/126948 | 11/2007 | |
| WO | WO 2012/054657 | 4/2012 | |
| WO | WO 2014/116832 | 7/2014 | |
| WO | WO 2014/131729 | 9/2014 | |
| WO | WO-2017195878 A1 * | 11/2017 | A61M 5/142 |

OTHER PUBLICATIONS

Catlin, Ann et al., Comparative analytics of infusion pump data across multiple hospital systems, Am. J. Health-System Pharm., vol. 72, pp. 317-324 (Feb. 15, 2015).

Chuk, Amanda et al., Utilizing Electronic Health Record Information to Optimize Medication Infusion Devices: A Manual Data Integration Approach, J. Healthcare Quality, pp. 1-9 (2014).

Syringe infusion Pumps with Dose Error Reduction Systems, Health Devices, pp. 33-43 (Feb. 2008).

International Search Report and Written Opinion, counterpart International Appl. No. PCT/EP2019/058493 (dated Jul. 26, 2019) (8 pages).

* cited by examiner

Master Drug Library > DRUG 2  Not for Human Use 1.0.0.90
DRUG 2

DRUG INFORMATION

Category            Created                          Last Modified
                    All User 05/13/2018 10:52 AM     All User 05/13/2018 10:52 AM DILUTIONS / CONCENTRATIONS                           Devices          Drug Libraries

| Number | Dilutions/Concentrations |                | DEVICE 1    | LIBRARY 1 |
|--------|--------------------------|
| 1      | 1mg/1mL (1mg/1mL)        |

ASSOCIATED THERAPIES

| DRUG 2 |
|---|
| Devices |
| DEVICE 1 |
| Dilutions/Concentrations |
| 1mg/1mL (1mg/1mL) |

FIG. 5

SYSTEMS AND METHODS FOR CONTROLLING A PLURALITY OF DRUG LIBRARIES

The present application is a U.S. National Stage of PCT International Patent Application No. PCT/EP2019/058493, filed Apr. 4, 2019, which claims benefit of U.S. Provisional Application No. 62/671,350, filed May 14, 2018, both of which are hereby incorporated herein by reference.

TECHNICAL FIELD

The present disclosure is generally directed to systems and methods for controlling a plurality of drug libraries, and in particular systems and methods for controlling a plurality of drug libraries on a plurality of patient devices, such as infusion pumps.

BACKGROUND

Infusion pumps are used to administer drugs and other medicaments to patients. For example, an infusion pump may administer a controlled amount of the medicament over time to the patient. The amount is administered pursuant to parameters entered by a clinician into the pump using a pump user interface.

Drug libraries are used on infusion pumps to provide further configuration beyond the software released by the manufacturer of the device. Drug libraries can include drug names, doses, and limits to the upper and/or lower ranges of administration parameters, for example. Conventionally, drug libraries may be maintained separately on each individual infusion pump.

While drug libraries are desirable, they pose certain challenges where a number of infusion pumps are owned, maintained and/or administered by a single entity. For example, if the limits to the upper and/or lower ranges of administration parameters for a particular drug are to be adjusted, then a change must be made to each drug library on each individual infusion pump. This represents a considerable amount of time and expense to the owner/administrator of the pumps. Further complications arise where user-configurable drug libraries are available. While desirable from the standpoint of the individual patient, such user-configurable drug libraries may cause inconsistencies to occur within the drug libraries maintained on different infusion pumps of a single entity.

SUMMARY

In a first aspect, a system for controlling a plurality of drug libraries includes a computing device on which is stored a master drug library, the master drug library comprising a plurality of drug definitions. The system also includes a plurality of programmable patient devices coupled to the server, each patient device having an individual drug library stored thereon, the individual drug library comprising a reference only to at least one of the drug definitions in the master drug library.

In a second aspect, a method for controlling a plurality of drug libraries includes storing on a computing device a master drug library, the master drug library comprising a plurality of drug definitions. The method also includes storing on each of a plurality of programmable patient devices an individual drug library, the individual drug library comprising a reference only to at least one of the drug definitions in the master drug library.

DESCRIPTION OF THE DRAWINGS

FIG. 5 is a simulated screenshot of a definition for one of the drugs within the master drug library.

DETAILED DESCRIPTION

A more detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

Figure 1:
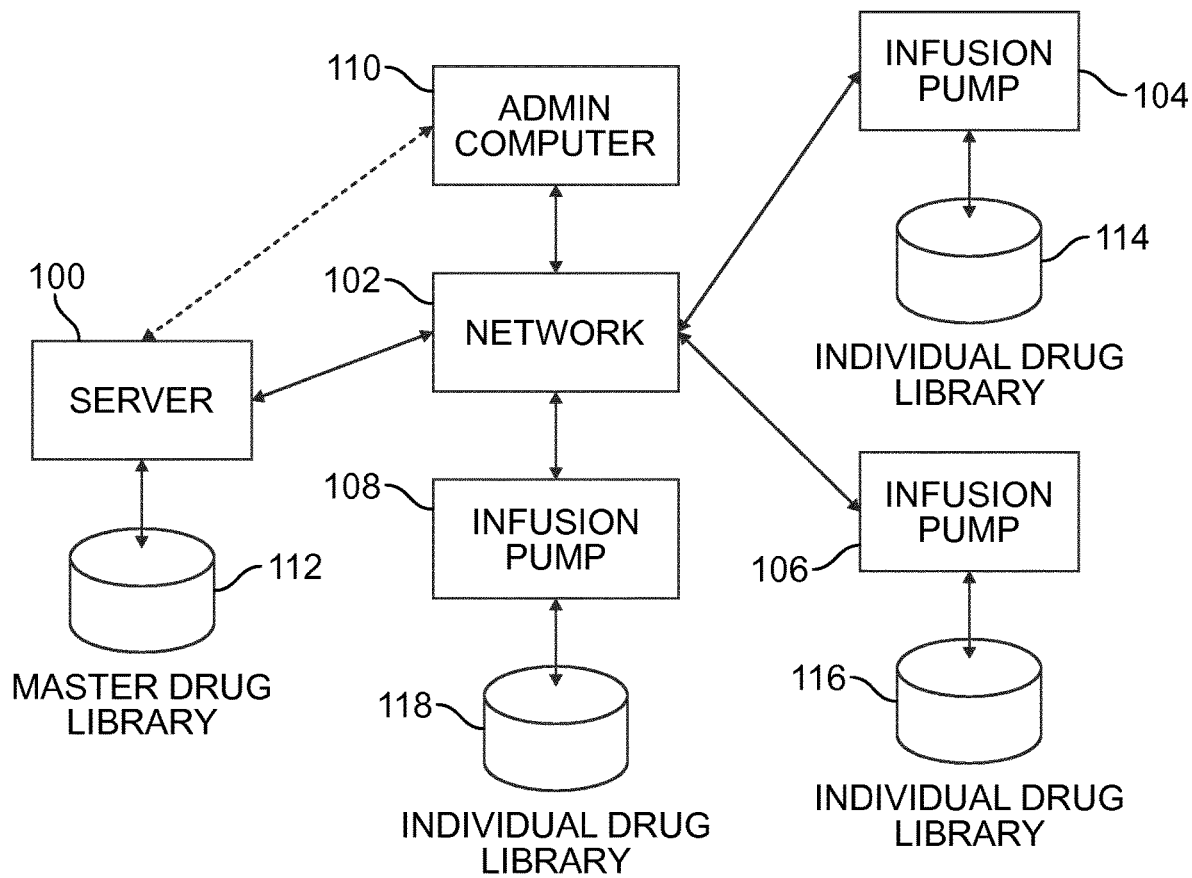
FIG. 1 is a schematic of a system including a server with a master drug library, an associated computer and a plurality of infusion pumps, each pump having its own individual drug library.

FIG. 1 illustrates a system of networked devices, including a computing device, such as a server, 100, a network 102 (which may include conventional equipment for defining a network, including servers, gateways, and routers, for example), and a plurality of patient devices, such as infusion pumps, 104, 106, 108. The system also includes a computer 110 that provides a user (e.g., an administrator) access to the server 100 to administer a master drug database 112 that resides on the server 100. As illustrated, the computer 110 may be coupled to the server 100 via the network 102, or optionally may have a more directly coupling to the server 100.

The server 100, the infusion pumps 104, 106, 108 and the computer 110 may include a microprocessor (which, in fact may include multiple physical and/or virtual processors). According to other embodiments, the server 100, the infusion pumps 104, 106, 108 and the computer 110 may include one or more electrical circuits designed to carry out the actions described herein. In fact, the server 100, the infusion pumps 104, 106, 108 and the computer 110 may include a microprocessor and other circuits or circuitry. In addition, the server 100, the infusion pumps 104, 106, 108 and the computer 110 may include one or more memories. The instructions by which the microprocessor is programmed may be stored on the one or more memories associated with the microprocessor, which memory/memories may include one or more tangible non-transitory computer readable memories, having computer executable instructions stored thereon, which when executed by the microprocessor, may cause the microprocessors to carry out one or more actions as described below.

Figure 2:
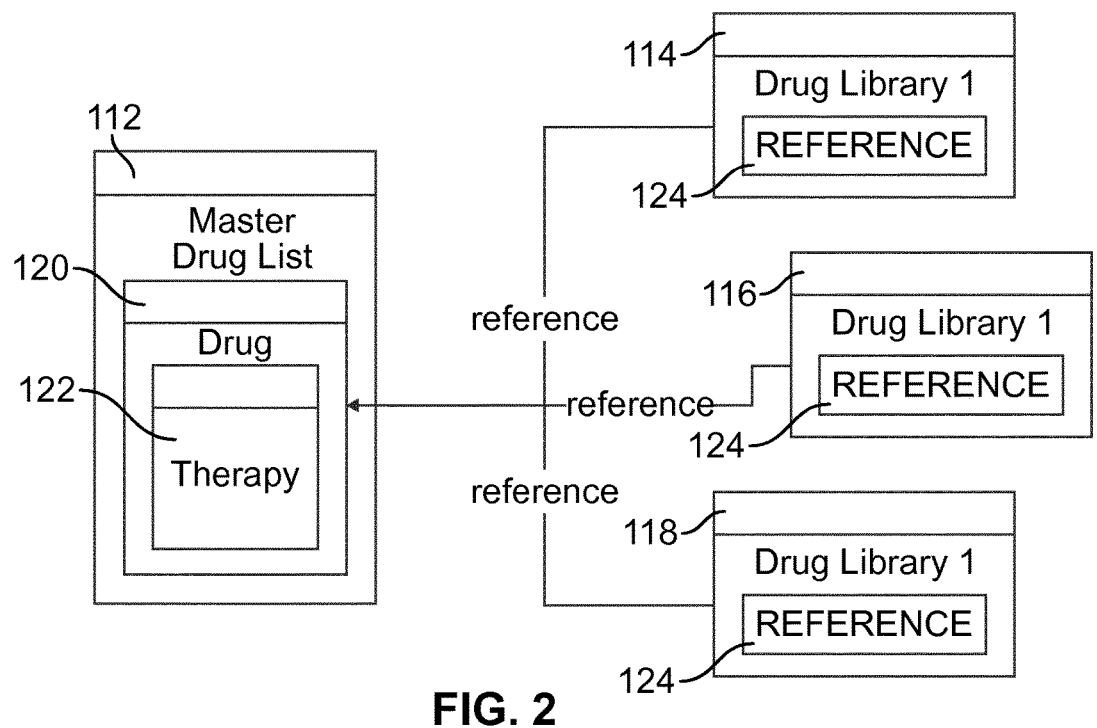
FIG. 2 is a schematic of the relationship between a master drug library, or list, which may be maintained on a server, for example, and a plurality of individual drug libraries, each of which may be maintained on an infusion pump, for example.

Each of the infusion pumps 104, 106, 108 has an individual drug library 114, 116, 118. The drug libraries 114, 116, 118 are associated to the master drug library 112 according to the methods described in greater detail in FIGS. 3 and 8. A general schematic of the association between the master drug library (or list) 112 and the individual drug libraries 114, 116, 118 is illustrated in FIG. 2. As illustrated in FIG. 2, the master drug library 112 includes a definition 120 for each drug, which definition 120 may have one or more definitions 122 associated therewith for each therapy associated with the drug. As illustrated in FIG. 2, the assignment of the drug (and associated therapies) to the individual drug libraries 114, 116, 118 occurs by adding a reference 124 (and only the reference 124) to the individual drug library 114, 116, 118 to the drug definition 120 of the drug in the master drug library 112.

The system and method described in general terms with reference to FIGS. 1 and 2 limits or eliminates duplication of data and information about drugs and their therapies that are included in each of the different individual drug libraries 114, 116, 118. Specifically, the master drug library 112 acts as a central repository in which all drugs and their therapies are defined. Once the required drugs and therapies have been defined, they can be added to individual drug libraries 114, 116, 118 by inclusion of a reference in the libraries 114, 116, 118. The inclusion of a reference in the libraries 114, 116, 118 limits or eliminates the need to copy and store the actual drug/therapy data in multiple places, thereby improving data integrity. In addition, changes made in the master drug library 112 will be applied to all of the individual drug libraries 112, 114, 116 because the master drug library represents a single source for this information.

The definition of the drug stored in the master drug library may include such identifying information as its name and concentration, for example. The number of drug definitions maintained in the drug library may be controlled by a system configuration parameter. Each drug definition may support one or more therapy definitions; it is also possible for a drug definition to support no therapy definitions. A therapy definition may include such identifying information as infusion modes, particular protocols, and limits on the infusion rates.

Figure 3:
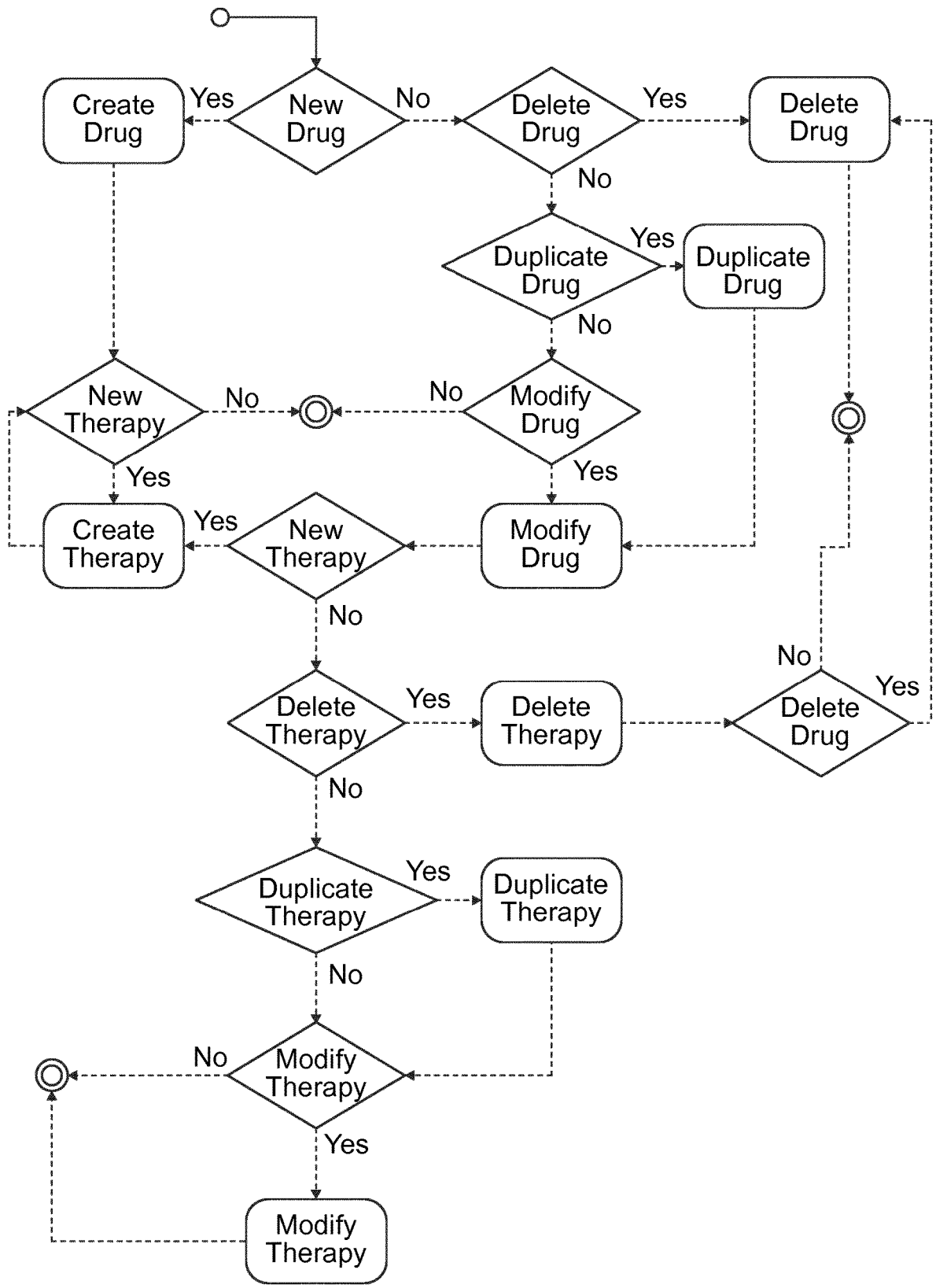
FIG. 3 is a flow chart illustrating a method of adding, modifying and deleting drug definitions and therapy definitions associated with a master drug library.

FIG. 3 illustrates a flow chart of how an administrator, via the computer 110, may add (create), modify, or delete a drug definition within the master drug library 112. Further, the flow chart of FIG. 3 illustrates how an administrator may add (create), modify or delete a therapy definition associated with one of the drug definitions.

Figure 4:
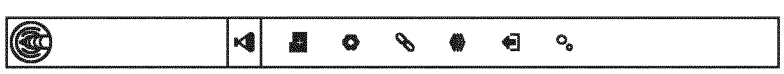
FIG. 4 is a simulated screenshot of a plurality of drug definitions maintained in the master drug library.

FIG. 4 illustrates how the information regarding the drug definitions included in one embodiment of a master drug library 112 may be displayed to a user, such as an administrator, via an electronic display device associated with the computer 110. In particular, the embodiment of the master drug library 112 includes a plurality of drug definitions, each identified by a drug name to the user. While a generic name has been used (e.g., "DRUG 1") for purposes of illustration in FIG. 4, the specific name of the drug may be used instead. In addition, information such as the number of drug libraries that refer to the drug definition and the number of therapy definitions associated with the drug definition may also be displayed, as has been included in FIG. 4.

FIG. 5 illustrates how the information regarding a particular drug definition (in this case, the definition for DRUG 2) may be displayed to a user, such as an administrator, via an electronic display device associated with the computer 110. In particular, the illustrated embodiment of the drug definition includes data regarding the dilutions or concentration of the drug, and the associated therapy definitions. In fact, the displayed information may also include information regarding the associated therapy definitions, such as the therapy definition displayed that includes data on the nature of the patient device (e.g., infusion device) and the dilutions/concentrations permitted. While a generic name has been used (e.g., "DEVICE 1") for purposes of illustration in FIG. 4, the specific name of the device may be used instead.

Figure 6:
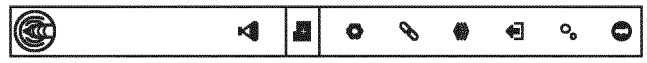
FIG. 6 is a simulated screenshot of a plurality of individual drug libraries associated by or to be associated by reference to a drug definition in the master drug library.
Figure 7:
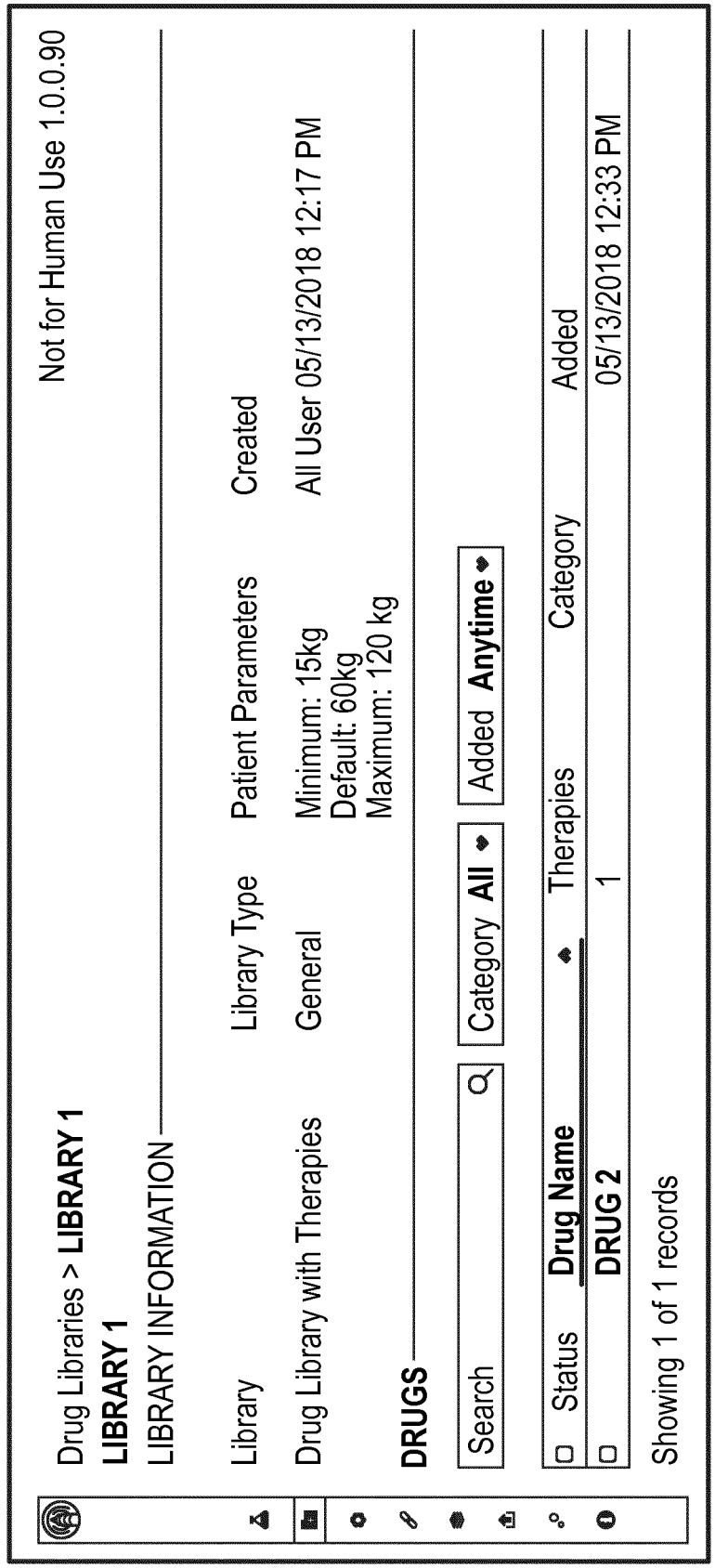
FIG. 7 is a simulated screenshot of one of the individual drug libraries and the drug definitions associated therewith.

Assuming that a particular drug definition is ready to be included in individual drug libraries, the user may define individual drug libraries including this drug definition. In this regard, FIG. 6 illustrates how a list of the available individual drug libraries may be displayed to the user, for example via an electronic display device associated with the computer 110. Again, while a generic name has been used (e.g., "LIBRARY 1") for purposes of illustration in FIG. 4, the specific name of the library may be used instead. The user may use an input device, such as a pointing device (e.g., a mouse) or a keyboard, to select one of the drug libraries. Additionally, FIG. 7 illustrates how the information on the individual drug library selected by the user may be displayed to the user, for example via an electronic display device associated with the computer 110. As is illustrated, the drug definitions available for association with an individual drug library 114, 116, 118 may be displayed, as well as some information regarding the associated therapy definitions (e.g., the number of such definitions). As noted above, once the reference 124 to a drug definition is added to an individual drug library 114, 116, 118, any updates made to the definitions of the drug or its associated therapies in the master drug library will be reflected immediately in all individual drug libraries that include reference to that drug definition. In a similar fashion, a reference to a therapy definition in an individual drug library will associate that therapy definition with the individual drug library.

Figure 8:
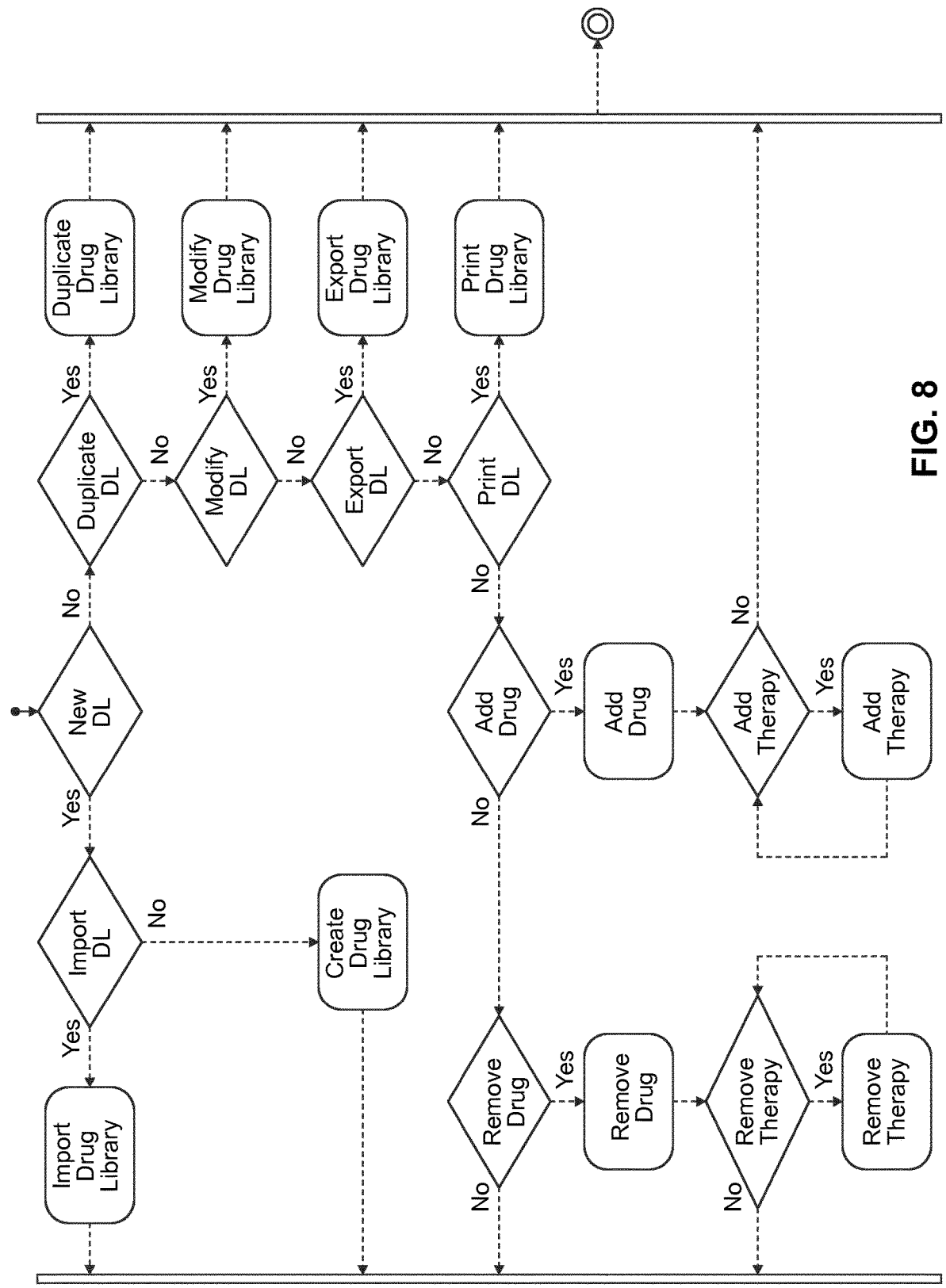
FIG. 8 is a flow chart illustrating the method of administrating individual drug libraries associated with a master drug library.

FIG. 8 illustrates a method of administering individual drug libraries associated with a master drug library. The method of FIG. 8 includes associating (by creating or by importing) the individual drug libraries, as well as modifying the individual drug libraries adding or removing drug definitions or therapy definitions to the individual drug library. The method further incudes other actions that may be taken relative to a particular individual drug library, such as duplicating the drug library, exporting the drug library, or printing an electronic or hard copy of the drug library.

The invention claimed is:

1. A system for controlling a plurality of drug libraries, the system comprising:
   a computing device on which is stored a master drug library, the master drug library comprising a plurality of drug definitions; and
   a plurality of programmable patient devices coupled to the computing device, each patient device having an individual drug library stored thereon,
   wherein the computing device is configured to assign a drug to the individual drug library by adding a reference only to at least one of the drug definitions in the master drug library.

2. The system of claim 1, wherein the master drug library comprises a first drug definition and a second drug definition, and the computing device is configured to assign a first drug and a second drug by adding a reference only to the first drug definition and a reference only to the second drug definition.

3. The system of claim 1, wherein the at least one of the drug definitions comprises at least one therapy definition.

4. The system of claim 1, wherein the computing device is configured to modify at least one of the plurality of drug definitions.

5. The system of claim 1, wherein the patient device comprises an infusion pump.

6. A method for controlling a plurality of drug libraries, the method comprising:
   storing on a computing device a master drug library, the master drug library comprising a plurality of drug definitions,
   storing on each of a plurality of programmable patient devices an individual drug library, and
   assign a drug to the individual drug library by adding a reference only to at least one of the drug definitions in the master drug library.

7. The method of claim 6, the master drug library comprising a first drug definition and a second drug definition, and assigning a drug to the individual drug library further comprising assigning a first drug by adding a reference only to the first drug definition and assigning a second drug by adding a reference only to the second drug definition.

8. The method of claim 6, wherein the at least one of the drug definitions comprising at least one therapy definition.

9. The method of claim 6, further comprising modifying at least one of the plurality of drug definitions.

10. The method of claim 9, wherein the at least one of the plurality of drug definitions comprising at least one therapy definition, and the modifying the at least one of the plurality of drug definitions comprises modifying the at least one therapy definition.

\* \* \* \* \*